US00PP36955P3

(12) United States Plant Patent
Kordes

(10) Patent No.: US PP36,955 P3
(45) Date of Patent: Sep. 16, 2025

(54) MINIATURE ROSE PLANT NAMED 'KORPOT126'

(50) Latin Name: *Rosa hybrida*
Varietal Denomination: KORpot126

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 18/989,326

(22) Filed: Dec. 20, 2024

(65) Prior Publication Data

US 2025/0221323 P1 Jul. 3, 2025

Related U.S. Application Data

(60) Provisional application No. 63/615,059, filed on Dec. 27, 2023.

(51) Int. Cl.
*A01H 6/74* (2018.01)
*A01H 5/02* (2018.01)

(52) U.S. Cl.
USPC ..... Plt./118
CPC ..... *A01H 6/749* (2018.05)

(58) Field of Classification Search
USPC ..... Plt./118
CPC ..... A01H 6/749; A01H 5/02
See application file for complete search history.

(56) References Cited

U.S. PATENT DOCUMENTS

| | | | |
|---|---|---|---|
| PP23,953 | P2 | 10/2013 | Kordes |
| PP29,649 | P3 | 9/2018 | Kordes |
| PP30,845 | P3 | 8/2019 | Kordes |

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'KORpot126', is described. The new variety forms in abundance on a substantially continuous basis yellow-colored blossoms. Blooms may continue year-round if grown inside a warm greenhouse. The vegetation is dark green colored, and the growth habit is compact. Ornamental foliage is formed.

1 Drawing Sheet

CROSS REFERENCE TO RELATED APPLICATIONS

This application claims priority to U.S. Provisional Application No. 63/615,059, which was filed on Dec. 27, 2023, the contents of which are hereby incorporated herein by reference for all purposes.

Latin name of genus and species of plant claimed: *Rosa hybrida.*

Variety denomination: 'KORpot126'.

STATEMENT REGARDING PRIOR DISCLOSURES BY THE INVENTOR

The first offer for sale of the new variety was February 2023, on the *Rosa Danica* website. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of miniature rose plant of the present invention was created by controlled breeding in 2018 in Offenseth-Sparrieshoop, Germany by artificial pollination wherein two parents were crossed which previously had been studied in the hope that they would contribute the desired characteristics. The female parent (i.e., the seed parent) of the new variety was an unnamed seedling which was the product of the cross between an unnamed seedling (not patented) and 'KORpot020' (U.S. Plant Pat. No. 23,953). The male parent (i.e., the pollen parent) of the new variety was the 'KORpot075' variety (U.S. Plant Pat. No. 29,649).

The parentage of the new variety can be summarized as follows:

(unnamed seedling x 'KORpot020') x 'KORpot075'

The seeds resulting from the above pollination were sown and small plants were obtained which were physically and biologically different from each other. Selective study resulted in the identification of a single plant of the new variety.

The new variety has been found to undergo asexual propagation at Klein Offenseth-Sparrieshoop, Germany by a number of routes such as vegetative cuttings. Asexual propagation techniques in Klein Offenseth-Sparrieshoop, Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of miniature rose plant of the present invention possesses the following combination of characteristics:

(a) forms yellow-colored blossoms, (b) exhibits a compact growth habit, and (c) provides dark green colored vegetation.

The new variety well meets the needs of the horticultural industry. It can be grown to advantage as ornamentation in parks, gardens, public areas, and residential landscapes. Accordingly, it is particularly well suited for growing in the landscape.

The new variety can be readily distinguished from its ancestors. More specifically, the seed parent (i.e., the product of (unnamed seedling x 'KORpot020')) displays a lower petal count and a smaller flower size compared to the new variety. Additionally, the new variety provides a yellow flower color, more petals, and larger sized flowers compared to the orange double flowers of the 'KORpot075' variety (i.e., the pollen parent). Moreover, the new variety can be readily distinguished from non-parental related similar varieties. For example, the 'KORpot080' variety (U.S. Plant Pat. No. 30,845) displays blossoms that are darker yellow in color with more petals compared to the new variety.

The new variety has been named the 'KORpot126' variety.

BRIEF DESCRIPTION OF THE PHOTOGRAPHS

The accompanying photograph shows, as nearly true as it is reasonably possible to make the same in a color illustration of this character, a typical specimen of the new variety and blossoms of the new variety. The illustrated rose plant of the new variety was approximately twelve weeks of age and was grown indoors on its own roots in a 10.5 cm container in Odense, Denmark in November 2022.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on a one-year-old specimen of the new variety, observed during September, while growing in a one-gallon container on its own roots in a greenhouse in Cochranville, Pennsylvania.

Botanical classification: *Rosa hybrida* cultivar 'KORpot126'.

Commercial classification: Miniature Rose.

Plant:

*Habit*.—Compact.

*Height*.—Approximately 35.0 cm on average from the top of the soil plane in a 1-gallon container.

*Width*.—Approximately 15.0 cm on average.

Branches:

*Stem color*.—Old wood: Green Group 138A young stems: Green Group 143A.

*Length*.—Main stems: approximately 35.0 cm on average. — secondary stems: approximately 15.0 cm on average.

*Diameter*.—Main stems: approximately 7.0 mm on average. — secondary stems: approximately 3.0 mm on average.

*Texture*.—Mostly glabrous with sparse prickles.

*Prickles*.—Amount: small, very few. — young prickles: length is approximately 3.0 mm on average; width is approximately 1.0 mm on average at point of attachment; and color is Yellow-Green Group N144A. — old prickles: length is approximately 5.0 mm on average; width is approximately 2.0 mm on average at point of attachment; and color is Greyed-Orange Group 166B.

Leaflets:

*Number*.—3, 5, and 7.

*Shape*.—Ovate; apex is acute; and base is rounded.

*Arrangement*.—Odd-pinnate.

*Margin*.—Serrate.

*Undulation*.—Slight.

*Glossiness of upper side*.—Matte.

*Texture*.—Upper surface: smooth. — under surface: smooth.

*Venation pattern*.—Reticulate.

*Size*.—Terminal leaflet: length is approximately 2.5 cm on average; width is approximately 1.5 cm on average. — lower leaflets: length is approximately 1.5 cm on average; width is approximately 1.2 cm on average. — 5Leaflet leaf: length is approximately 5.5 cm on average; width is approximately 3.5 cm on average.

Foliage:

*Young foliage*.—Upper surface color: Green Group 138A with indistinguishable venation. — under surface color: Yellow-Green Group 146C with indistinguishable venation.

*Old foliage*.—Upper surface color: Green Group 137A with indistinguishable venation. — under surface color: Green Group 137A with indistinguishable venation.

*Petiole*.—Texture: upper surface is mostly smooth with sparse prickles; under surface is mostly smooth with sparse prickles. — length: approximately 2.0 cm on average. — width: approximately 2.0 mm on average. — upper surface color: Green Group 143C. — under surface color: Green Group 143C.

*Rachis*.—Length: approximately 1.0 cm on average. — width: approximately 1.0 mm on average. — upper surface color: Green Group 137D. — under surface color: Green Group 137D.

*Stipules*.—Length: approximately 5.0 mm on average. — width: approximately 2.0 mm on average. — margin: entire to erose. — upper surface color: Green Group 143C. — lower surface color: Green Group 143C.

Inflorescence:

*Number of flowers*.—About 15 to 20 blooms on average on a plant at once.

*Number of blossoms per stem or in a cluster*.—Typically 1 bloom per stem on average.

*Peduncle*.—Color: Green Group 143A. — diameter: approximately 3.0 mm on average. — length: approximately 3.0 cm on average. — surface texture: glabrous.

*Sepals*.—Number: 5. — upper surface color and texture: Green Group 143C, covered in short pubescence. — under surface color and texture: Green Group 143C, puberulent. — size: length is approximately 1.8 cm on average; width is approximately 5.0 mm on average. — margin: entire with occasional extensions on two or three sepals measuring approximately 2.0 mm in length and 1.0 mm in width on average with moderate/medium undulation. — shape: lanceolate. — apex: acute to aristate. — base: truncate or flat as it joins the receptacle.

*Buds*.—Shape: ovoid. — size: length is approximately 1.5 cm on average; width is approximately 1.0 cm on average. — color (when opening): Yellow Group 8A.

*Flower*.—Form: double, rosette. — profile: flat. — diameter: approximately 3.5 cm on average. — height: approximately 1.0 cm on average. — duration: on the plant approximately 16 days. — petal color when first and fully opened: upper surface is Yellow-Orange Group 17A with edges of Yellow Group 8C; under surface is Yellow Group 8A; and a basal spot of Yellow Group 7A. — petal color at end of bloom: upper surface is Yellow Group 8C; under surface is Yellow Group 8C; and a basal spot of Yellow Group 7B. — petals reflex one by one: yes.

*Fragrance*.—None noticeable.

*Petal*.—Number: 25 to 30 on average. — drop: average for the type. — length: inner petals typically 1.0 cm; outer petals typically 2.0 cm. — width: inner petals typically 5.0 mm; outer petals typically 2.0 cm. — overall shape: broadly obovate. — margin: entire with medium undulation. — apex shape: rounded to cuspidate. — base shape: rounded to cuneate. — texture: upper surface is glabrous; under surface is glabrous.

*Petaloids*.—Number: 3 to 5. — length: approximately 7.0 mm on average. — width: approximately 3.0 mm on average. — color: Yellow Group 13A with no distinguishable basal spot. — texture: smooth. — margin: variable, entire to erose. — shape: rounded and mostly curving inward. — apex: rounded. — base: cuneate.

*Stamen*.—Number: approximately 45 to 50. — anthers: number is approximately 45 to 50; color is Yellow Group 8A; length is approximately 1.5 mm on average; and shape is oval. — filaments: length is approximately 2.0 mm on average and color is Yellow-Orange Group 15A.

*Pistils*.—Arrangement: separate and free. — number: approximately 35. — style: length is approximately 5.0 mm on average and color is Greyed-Orange Group 176A. — stigma: diameter is less than 1.0 mm on average; shape is fan shaped; color is Greyed-Orange Group 176A.

*Receptacle*.—Diameter: approximately 4.0 mm on average. — depth: approximately 7.0 mm on average. — shape: urn shaped. — color: Yellow-Green Group 144A. — surface texture: smooth.

*Pollen*.—Amount: none observed.

*Hips/seed*.—None observed.

Development:

*Vegetation*.—Dark green and vigorous.

*Blossoming*.—Abundant and continuous; blooms may continue year-round if grown inside a warm greenhouse.

*Resistance to diseases*.—Good resistance for powdery mildew (*Sphaerotheca pannosa*) under normal greenhouse growing conditions in Cochranville, Pennsylvania.

*Hardiness*.—Unknown.

The new 'KORpot126' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of miniature rose plant named 'KORpot126' characterized by the following combination of characteristics:

(a) forms yellow-colored blossoms, (b) exhibits a compact growth habit, and (c) provides dark green colored vegetation;

substantially as herein shown and described.

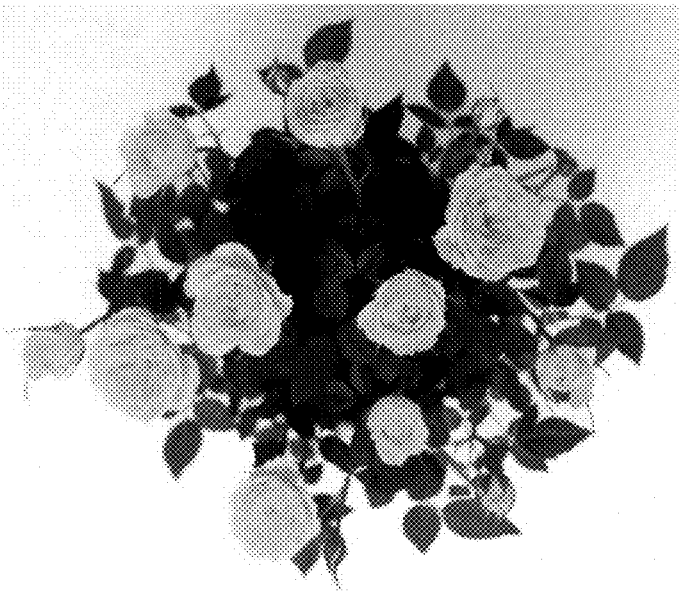

* * * * *